(12) United States Patent
Maimon et al.

(10) Patent No.: US 12,070,388 B2
(45) Date of Patent: *Aug. 27, 2024

(54) ACTIVE INTRODUCER SHEATH SYSTEM

(71) Applicant: EDWARDS LIFESCIENCES CORPORATION, Irvine, CA (US)

(72) Inventors: David Maimon, Atlit (IL); Liron Tayeb, Peduel (IL); Eran Goldberg, Nesher (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/138,651

(22) Filed: Apr. 24, 2023

(65) Prior Publication Data
US 2023/0255770 A1 Aug. 17, 2023

Related U.S. Application Data

(63) Continuation of application No. 17/359,332, filed on Jun. 25, 2021, now Pat. No. 11,633,280, which is a continuation of application No. 16/111,951, filed on Aug. 24, 2018, now Pat. No. 11,051,939.

(60) Provisional application No. 62/552,609, filed on Aug. 31, 2017.

(51) Int. Cl.
*A61F 2/24* (2006.01)
*A61M 25/00* (2006.01)
*A61F 2/95* (2013.01)

(52) U.S. Cl.
CPC .......... *A61F 2/2439* (2013.01); *A61F 2/2427* (2013.01); *A61F 2/2433* (2013.01); *A61M 25/0023* (2013.01); *A61F 2/9517* (2020.05); *A61M 2025/0024* (2013.01)

(58) Field of Classification Search
CPC .. A61M 2025/0024; A61M 2025/0025; A61M 25/0021; A61M 25/0023
See application file for complete search history.

(56) References Cited

U.S. PATENT DOCUMENTS 6,338,730 B1 * 1/2002 Bonutti ................. A61M 25/04
604/509

* cited by examiner

*Primary Examiner* — Majid Jamialahmadi
(74) *Attorney, Agent, or Firm* — Meunier Carlin Curfman LLC; Joel B. German (57) ABSTRACT

The active introducer sheath systems disclosed herein are expanded by activating a translation mechanism at the handle. The sheath has an inner cylindrical structure of comingled fixed and mobile elongate rods bound together by an attachment line. Activating the translation mechanism causes the mobile rods to move axially with respect to the fixed rods, changing the internal tension in the attachment line. Increased tension draws the fixed and mobile rods closer together, decreasing the diameter of the cylindrical structure. Decreased tension in the attachment line enables the fixed and mobile rods to move apart, increasing the diameter of the cylindrical structure. A prosthetic device, such as a prosthetic heart valve, can be routed through the expanded sheath and to the implantation site. During implantation, the sheath can be contracted back to its original outer diameter, and expanded again for retrieval of the delivery apparatus.

20 Claims, 7 Drawing Sheets

ACTIVE INTRODUCER SHEATH SYSTEM

CROSS REFERENCE TO RELATED APPLICATIONS

This application is a continuation of U.S. application Ser. No. 17/359,332, filed Jun. 25, 2021, which is a continuation of U.S. application Ser. No. 16/111,951, filed Aug. 24, 2018, which claims the benefit of U.S. Provisional Application No. 62/552,609, filed Aug. 31, 2017. Each of the aforementioned applications is incorporated by reference in its entirety for all purposes.

FIELD

The present application is directed to an active introducer sheath system for use with catheter-based technologies for repairing and/or replacing heart valves, as well as for delivering an implant, such as a prosthetic valve to a heart via the patient's vasculature.

BACKGROUND

Endovascular delivery catheter assemblies are used to implant prosthetic devices, such as prosthetic valves, at locations inside the body that are not readily accessible by surgery or where access without invasive surgery is desirable. For example, aortic, mitral, tricuspid, and/or pulmonary prosthetic valves can be delivered to a treatment site using minimally invasive surgical or transcatheter techniques.

An introducer system can be used to safely introduce a delivery apparatus into a patient's vasculature (e.g., the femoral artery). An introducer system generally has an elongated introducer sheath that is inserted into the vasculature and a handle that contains one or more sealing valves that allow a delivery apparatus to be placed in fluid communication with the vasculature with minimal blood loss. Once the introducer sheath is positioned within the vasculature, the shaft of the delivery apparatus is advanced through the sheath and into the vasculature, carrying the prosthetic device. Introducer systems can be used in the delivery of prosthetic devices in the form of implantable heart valves, such as balloon-expandable implantable heart valves. An example of such an implantable heart valve is described in U.S. Pat. No. 5,411,552 entitled "Valve Prosthesis for Implantation in the Body and a Catheter for Implanting such Valve Prosthesis," and also in U.S. Pat. No. 9,393,110 entitled "Prosthetic Heart Valve," both of which are hereby incorporated by reference. The introducer systems can also be used with the delivery systems for other types of implantable devices, such as self-expanding and mechanically-expanding implantable heart valves, stents or filters.

Conventional methods of accessing a vessel, such as a femoral artery, prior to introducing the delivery apparatus include dilating the vessel using multiple dilators or sheaths that progressively increase in diameter. This repeated insertion and vessel dilation can increase the amount of time the procedure takes, as well as the risk of damage to the vessel. Expandable introducer sheaths, formed of highly elastomeric materials, allow for the dilating of the vessel to be performed by the passing prosthetic device. U.S. Pat. No. 8,790,387, entitled "Expandable Sheath for Introducing an Endovascular Delivery Device into a Body" and incorporated herein by reference, discloses a sheath with a split outer polymeric tubular layer and an inner polymeric layer. A portion of the inner polymeric layer extends through a gap created by the cut and can be compressed between the portions of the outer polymeric tubular layer. Upon expansion of the sheath, portions of the outer polymeric tubular layer separate from one another, and the inner polymeric layer is expanded to a substantially cylindrical tube. Advantageously, the sheath disclosed in the '387 patent can locally and temporarily expand for passage of implantable devices and then return to its starting diameter. This expansion is passive in nature, in that it is not directly controlled by the practitioner performing the procedure. The passive expansion occurs due to the pressure that the passing implantable device places on the inner surfaces of the sheath.

There remains a need for further improvements in expandable introducer sheaths for endovascular systems used for implanting valves and other prosthetic devices.

SUMMARY

The active introducer sheath systems disclosed herein allow a practitioner to actively initiate the expansion of the sheath at any time during the procedure, separate from the passing of the delivery system. The sheath is expanded by activating a translation mechanism at the handle of the introducer sheath system. The sheath has an inner cylindrical structure of comingled fixed and mobile elongate rods bound together by an attachment line, such as an attachment wire, that extends around the rods. Proximal portions of the fixed rods are fixedly attached to the handle, whereas proximal portions of the mobile rods are attached to the translation mechanism of the handle. Activating the translation mechanism causes the mobile rods to move axially with respect to the fixed rods, changing the internal tension in the attachment wire. Increased tension draws the fixed and mobile rods closer together, decreasing the diameter of the cylindrical structure. On the other hand, relaxing the tension in the attachment wire enables the fixed and mobile rods to move apart, increasing the diameter of the cylindrical structure. This active expansion mechanism allows the practitioner to precisely control the outer diameter during both expansion and contraction of the sheath.

The active introducer sheath systems can also include an outer cover extending around the inner cylindrical structure. The outer cover can be formed of, or include, an elastomeric or a non-elastomeric material.

In some embodiments, each fixed rod of the inner cylindrical structure is positioned adjacent to a mobile rod. The inner cylindrical structure can include, for example, 2, 3, 4, 5, or 6 elongate fixed rods. The elongate mobile rods and the elongate fixed rods can be formed of, or can include, metal materials or polymer materials.

The elongate rods are bound together by one or more attachment lines that extend around the rods. The attachment line or lines can be, for example, metal wires or polymer bands. In some embodiments, the attachment lines can include at least one flat outer surface to assist with bending. The attachment lines can be structured as a plurality of rings, where each ring connects the elongate rods of the inner cylindrical structure. Alternatively, one or more attachment lines can form a coil to connect the elongate rods of the inner cylindrical structure. For example, the attachment lines can be threaded through the elongate rods, or they can be attached to outer surfaces of the elongate rods. In either case, the attachment of the elongate rod to an attachment line forms a connection point. The attachment line can be welded, crimped, or bonded to an elongate rod at a given connection point. In some embodiments, the attachment line or lines can also be attached to the outer cover.

The translation mechanism of the handle can include a screw mechanism. For example, the screw mechanism can include a rotating nut that is attached to the set of mobile rods and threaded around the handle such that it is axially movable along the handle. In some embodiments, each elongate mobile rod is attached at its proximal end to a sliding ring which encircles the handle and engages the rotating nut, for example, via an interlocking connection feature extends circumferentially around the handle. The sliding ring, which is positioned distally to the rotating nut, translates axial movement from the rotation of the nut to the mobile rods.

Methods of moving prosthetic devices through an active introducer sheath system, for example, to deliver a prosthetic heart valve to a patient, are disclosed. When performing a minimally invasive procedure, the active introducer sheath system is inserted into a patient, for example, into the femoral artery, prior to activating the translation mechanism to initiate sheath expansion. Activating the translation mechanism can be performed, in some embodiments, by rotating a screw mechanism, which pushes or pulls the set of elongate mobile rods axially with respect to the set of elongate fixed rods. The movement of the mobile rods with respect to the fixed rods lowers an internal tension in the attachment lines of the inner cylindrical structure, allowing the inner cylindrical structure to expand in diameter. The prosthetic device can then be pushed through the expanded inner cylindrical structure. The inner cylindrical structure can be contracted after pushing the prosthetic device through by moving the set of mobile rods in a reverse direction via the translation mechanism. In some embodiments of the method, the inner cylindrical structure expands to the extent that its inner diameter is wider than the greatest outer diameter of the passing prosthetic device. Upon contraction, the outer diameter of the inner cylindrical structure can be returned to an original outer diameter.

DETAILED DESCRIPTION

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" as used herein refer to regions of a sheath, catheter, or delivery assembly. "Proximal" means that region closest to handle of the device, while "distal" means that region farthest away from the handle of the device.

"Axially" or "axial" as used herein refers to a direction along the longitudinal axis of the sheath.

The disclosed active introducer sheath systems minimize trauma to the blood vessel during the delivery of a prosthetic device. During a transcatheter procedure, insertion and expansion of the introducer sheath causes the vessel walls to stretch radially, while insertion of the prosthetic device through the introducer causes the vessel walls to stretch longitudinally. When a passing prosthetic device stretches the sheath, the vessel walls are stretched in both directions simultaneously, which can lead to tearing. Disclosed embodiments of the active introducer sheath systems allow a practitioner to actively initiate the expansion of the sheath at any time during the procedure, separate from the passing of the delivery system. Tearing risk is minimized because longitudinal stretching occurs separately from radial stretching. The sheath is expanded by activating a translation mechanism at the handle of the introducer sheath system. The sheath has an inner cylindrical structure of comingled fixed and mobile elongate rods bound together by an attachment line, such as an attachment wire, that extends around the rods. Proximal portions of the fixed rods are attached to the handle, whereas proximal portions of the mobile rods are attached to the translation mechanism of the handle. Activating the translation mechanism causes the mobile rods to move axially with respect to the fixed rods, changing the internal tension in the attachment wire. Increased tension draws the fixed and mobile rods closer together, decreasing the diameter of the cylindrical structure. On the other hand, relaxing the tension in the attachment wire enables the fixed and mobile rods to move apart, increasing the diameter of the cylindrical structure. This active expansion mechanism allows for precise control over the outer diameter during both expansion and contraction of the sheath. Push force, or the force it takes to advance the prosthetic device through the sheath, is minimized because the prosthetic device itself is not responsible for expanding the sheath, further reducing potential trauma to the vessel walls.

Figure 1:
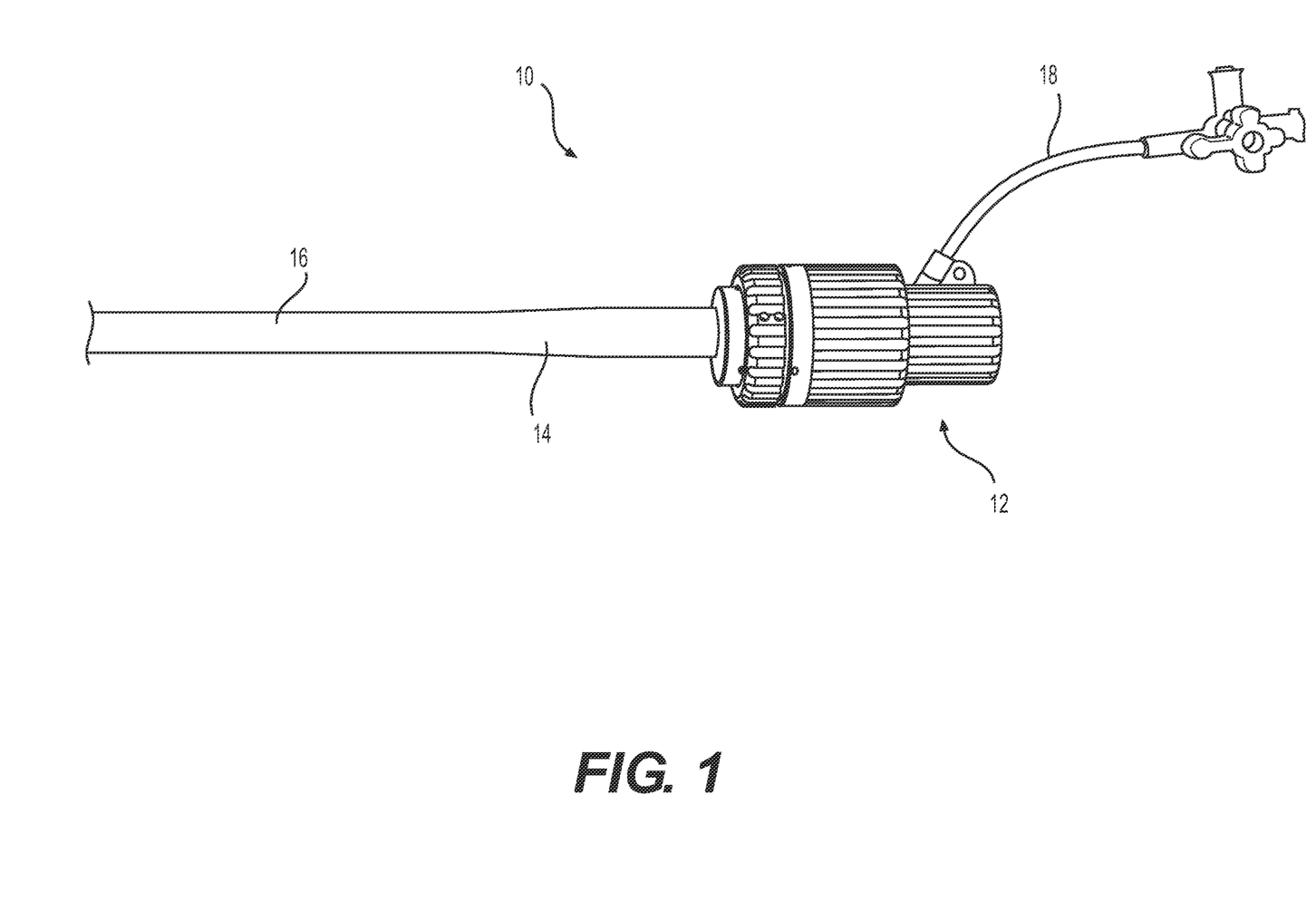
FIG. 1 shows an embodiment of an active introducer sheath system.

FIG. 1 illustrates the proximal end of an active introducer sheath system 10 according to the present disclosure. The introducer sheath system 10 is configured for use with a delivery apparatus 110 to deliver a prosthetic implant, such as a prosthetic heart valve, to a patient. For example, the shaft 122 of the representative delivery apparatus 110 shown in FIG. 2 can be inserted through the handle 12 and sheath 14 of introducer sheath system 10 to deliver a prosthetic device to a patient. It should be understood that the delivery apparatus 110 described herein is exemplary only, and that other similar delivery systems can of course be used with the introducer sheath system 10.

As outlined above, the sheath 14 includes an inner cylindrical structure 20 of comingled fixed and mobile elongate rods bound together by an attachment line that extends around the rods. An outer cover 16 extends around the inner cylindrical structure 20 comprising the mobile rods. In FIG. 1, only the outer cover 16 of the sheath 14 is visible. The outer cover 16 can be formed of an elastomeric material, such as silicone or urethane, for example. An elastomeric outer cover 16 will stretch to conform to the expansion state of the underlying inner cylindrical structure 20. Alternatively, the outer cover 16 can be formed of a non-elastomeric material, such as dyneema membrane, polyether ether ketone (PEEK), or polyethylene terephthalate (PET). A non-elastomeric outer cover 16 has excess material that will wrinkle or fold when the underlying inner cylindrical structure 20 is in a contracted state.

In some embodiments, the sheath 14 has an inner diameter of about 2.7 millimeters (8 French) when contracted, and an inner diameter of about 8.0 millimeters (24 French) when expanded. In some embodiments, the sheath 14 has an outer diameter of about 4.3 millimeters (13 French) when contracted and about 8.5 millimeters (26 French) when expanded. In some embodiments, the wall thickness of the sheath 14 is from about 0.6 to about 1.6 millimeters when contracted, and from about 0.2 to about 0.5 millimeters when expanded. However, the dimensions of the sheath can vary. The numerical values given above to describe a sheath embodiment are not meant to limit the scope of the disclosure.

Figure 2:
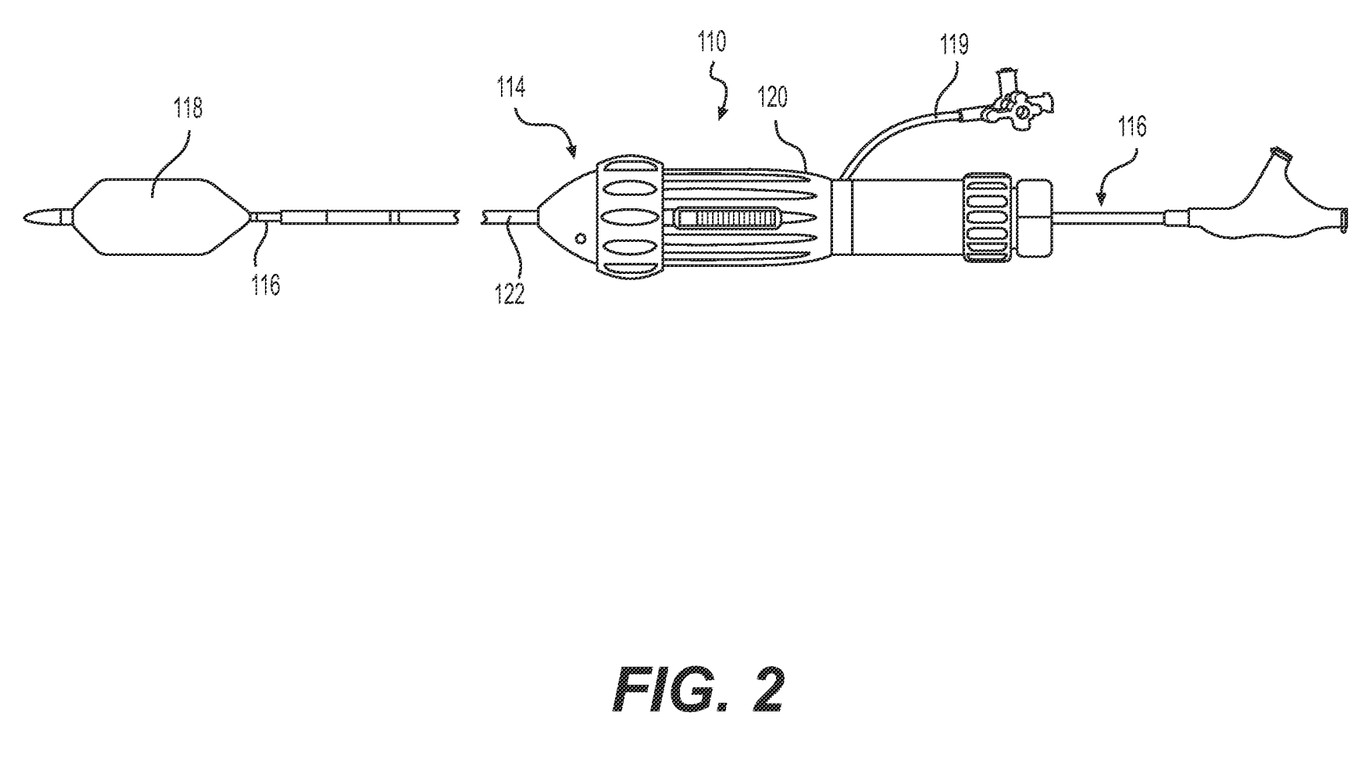
FIG. 2 shows an embodiment of a delivery apparatus.

The introducer sheath system 10 has a central lumen extending through its handle 12 and sheath 14. At a proximal end of the central lumen, the introducer sheath system 10 includes a hemostasis valve that prevents leakage of pressurized blood. Generally, during use a distal end of the sheath 14 is passed through the skin of the patient and inserted into a vessel, such as the femoral artery. The shaft 122 of a delivery apparatus 110, such as the one shown in FIG. 2, is then inserted into the introducer sheath system 10 through the proximal hemostasis valve, and advanced through the patient's vasculature to deliver the prosthetic device to the patient. Flush tubing 18 is attached to the introducer sheath system 10, and is used to fill the system with saline or another physiologically balanced solution prior to advancing the sheath 14 into the patient, ensuring no air bubbles are introduced to the bloodstream.

The representative delivery apparatus 110 shown in FIG. 2 includes a steerable guide catheter 114, which includes a handle portion 120 coupled to an elongated shaft 122. A balloon catheter 116 extends through the handle portion 120 and the shaft 122 of the guide catheter 114, and is in fluid communication with balloon 118. The guide catheter 114 and the balloon catheter 116 illustrated in FIG. 2 are adapted to slide longitudinally relative to each other to facilitate delivery and positioning of a prosthetic heart valve at an implantation site in a patient's body. In FIG. 2, balloon 118 is depicted in an inflated state, but it is understood that balloon 118 is deflated during advancement through the introducer sheath system 10 and the patient's vasculature. A prosthetic heart valve or other prosthetic device can be crimped onto balloon 118 for delivery to the procedure site. The delivery apparatus 110 also includes flush tubing 119 to prevent air bubbles from entering the bloodstream.

Figure 3A:
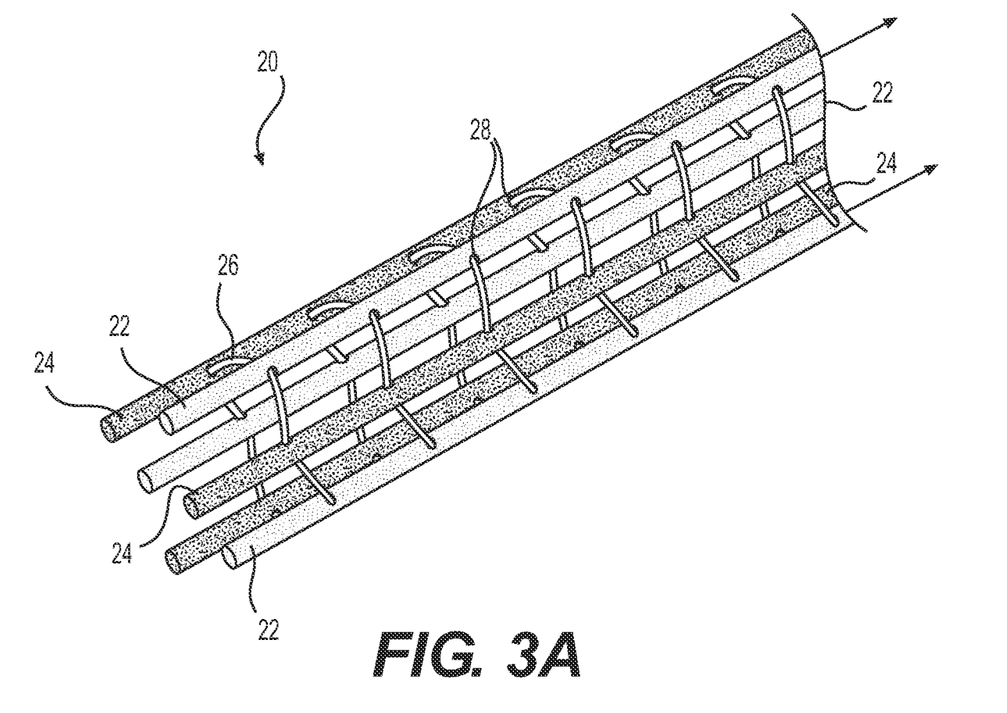
FIG. 3A shows a perspective view of an expanded inner cylindrical structure of an embodiment of the active introducer sheath system.

FIG. 3A is a perspective view of the inner cylindrical structure 20 of sheath 14 in its expanded state. Proximal portions of three cylindrically arranged fixed rods 24 are fixedly attached at handle 12, which is not shown in FIG. 3A. Proximal portions of three mobile rods 22 are attached, either directly or indirectly, to the translation mechanism of the handle 12, which will be described in more detail below (in reference to FIGS. 6 and 7). The mobile and fixed rods 22, 24 are comingled, such that each fixed rod 24 is adjacent a mobile rod 22. One or more attachment lines 26 extend through the comingled mobile and fixed rods 22, 24, binding the rods together and maintaining the cylindrical shape along the length of the sheath 14.

Figure 3B:
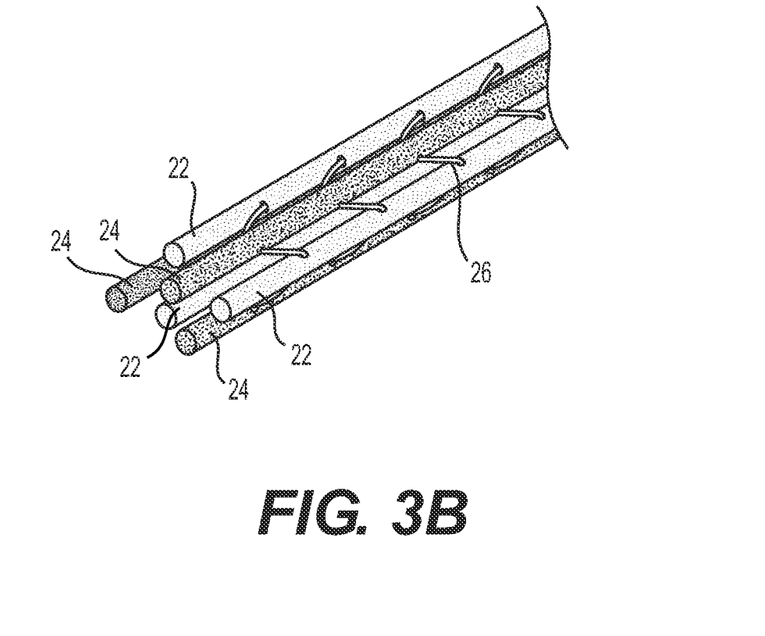
FIG. 3B shows a perspective view of the inner cylindrical structure of FIG. 3A in a contracted state.
Figure 4A:
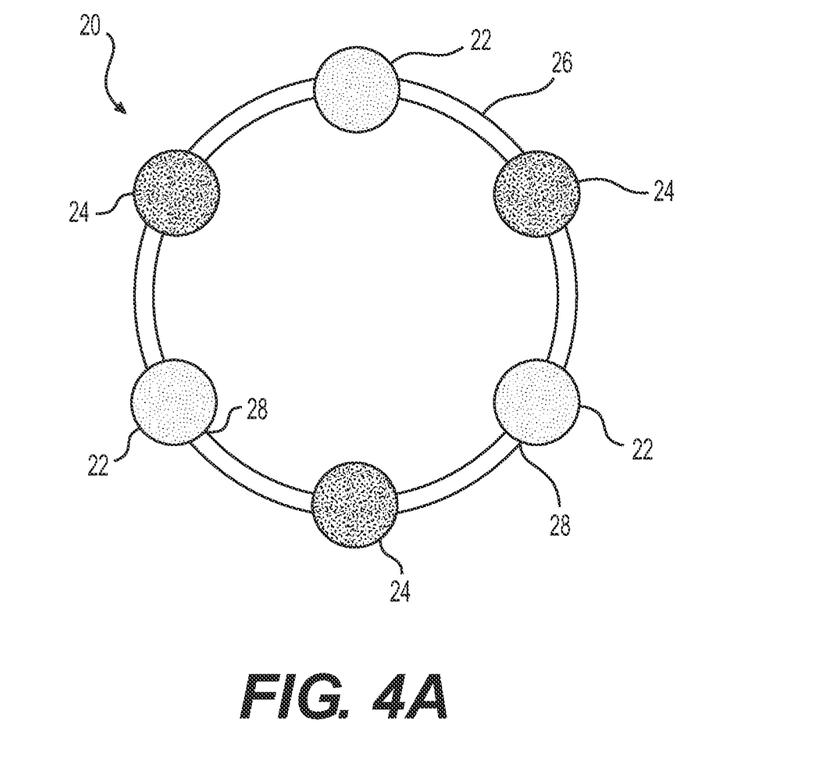
FIG. 4A shows a cross sectional view of an expanded inner cylindrical structure of an embodiment of the active introducer sheath system.
Figure 4B:
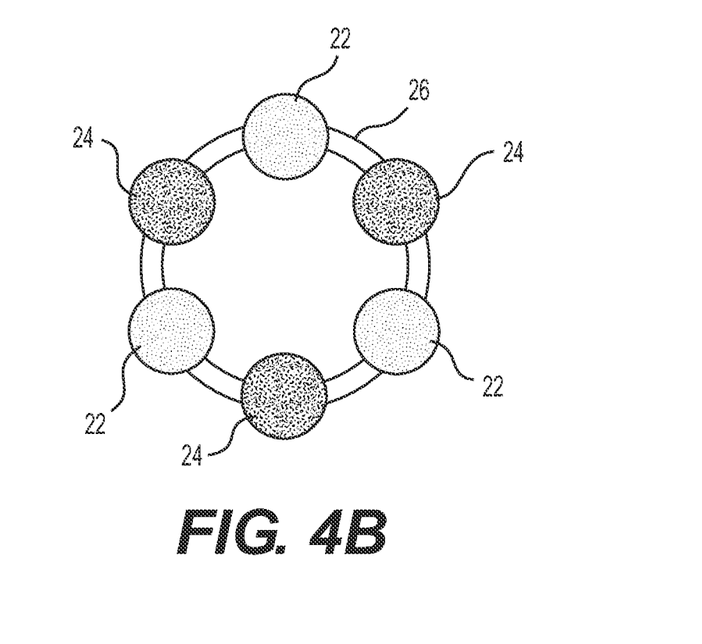
FIG. 4B shows a cross sectional view of the inner cylindrical structure of FIG. 4A in a contracted state.
Figure 5A:
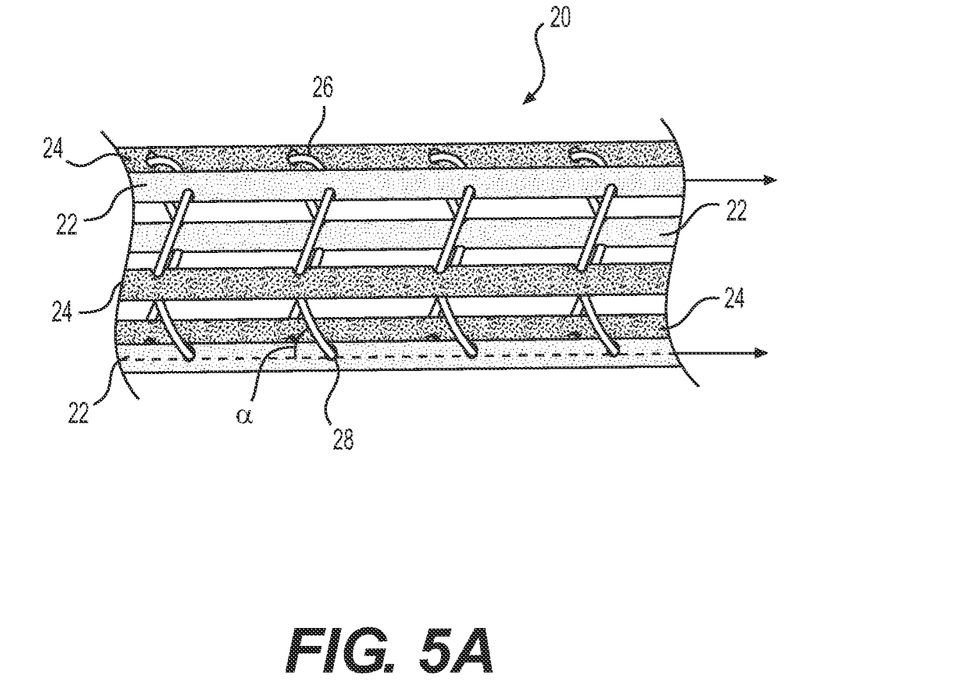
FIG. 5A shows a side view of an expanded inner cylindrical structure of an embodiment of the active introducer sheath system.
Figure 5B:
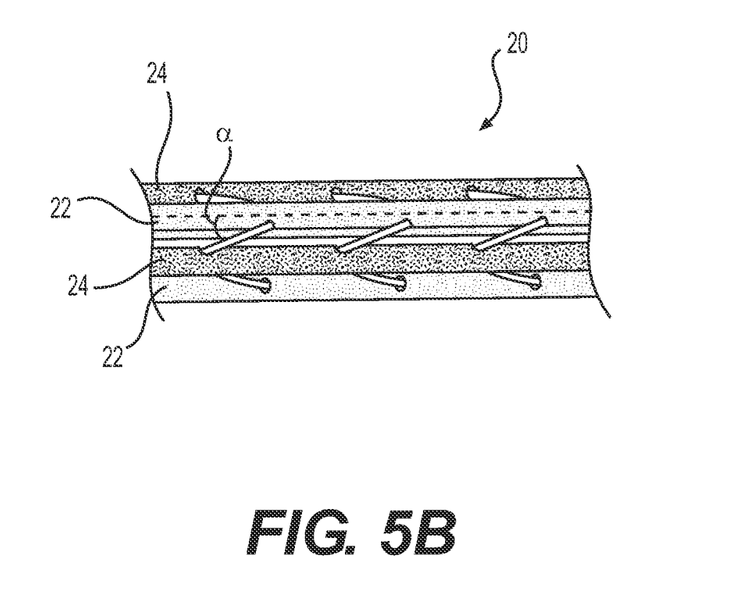
FIG. 5B shows a side view of the inner cylindrical structure of FIG. 5A in a contracted state.

Upon activation of the translation mechanism 34 at handle 12 (FIG. 6), the mobile rods move axially in the direction of the arrows shown in FIG. 3A. Because of the stationary position of the fixed rods 24, the movement of the mobile rods 22 increases the internal tension in the attachment line 26, which draws the mobile and fixed rods 22, 24 closer together, changing their radial locations and decreasing the diameter of the inner cylindrical structure 20, as shown in FIG. 3B. The cross-sectional diagram of FIG. 4A shows the inner cylindrical structure 20 in its expanded state, whereas FIG. 4B shows the inner cylindrical structure 20 in its contracted state. The distance between adjacent mobile and fixed elongate rods 22, 24 decreases as the overall diameter of the inner cylindrical structure decreases. FIGS. 5A and 5B show a side view of an expanded and collapsed inner cylindrical structure 20, respectively. The attachment angle, α, made at connection points 28 between the attachment line 26 and the longitudinal axis of an elongate rod, decreases as the mobile rods 22 are translated axially with respect to the fixed rods 24. The expansion rate of sheath 14 changes as the attachment angle α gets larger or smaller.

The elongate mobile and fixed rods 22, 24 can be formed of polymer materials or from metal materials such as, for example, stainless steel, nitinol, or cobalt-chromium. The number of rods can be varied to alter the expansion rate of sheath 14. While the embodiments depicted in FIGS. 3-5 show a total of six elongate rods, it is understood that the inner cylindrical structure 20 can have as few as four total rods (two mobile and two fixed) or as many as twelve total rods (six mobile and six fixed). The elongate mobile and fixed rods 22, 24 may be cylindrical, as depicted in FIGS. 3-5, or they may be rectangular/linear for increased rigidity. In some embodiments, the elongate rods 22, 24 can be from about 0.5 to about 1.2 millimeters thick in a direction perpendicular to their longitudinal axis. This size range provides structural rigidity while minimizing the wall thickness of the inner cylindrical structure 20. However, the rods may be other thicknesses without deviating from the scope of the disclosure.

The attachment line 26 is depicted in FIGS. 3-5 as being threaded through the elongate rods 22, 24. Alternatively, the attachment line 26 could extend around the outside or inside of elongate rods 22, 24. The attachment line 26 attaches to each elongate rod at a series of connection points 28. The attachment line 26 can be welded to each rod, crimped to each rod, or bonded to each rod using a bonding agent, such as a glue or other adhesive compound. In some embodiments, the attachment line 26 can be attached by different methods at different connection points 28. The attachment line 26 can be structured as a series of discrete rings that connect the mobile and fixed rods 22, 24. For example, as shown in FIGS. 3-5, each ring extends around or through each mobile rod 22 and each fixed rod 24 at connection points 28. Alternatively, part or all of the attachment line 26 can be structured as a continuous coil that connects each mobile rod 22 and each fixed rod 24, e.g., by winding around or through the mobile and fixed rods 22, 24. Some embodiments may have a flat attachment line 26, meaning an attachment line that includes at least one flat outer surface, which can facilitate bending to ease the radial expansion.

The thickness and rigidity of the attachment line 26 are balanced to provide substantial strength to the inner cylindrical structure 20 while maximizing the mobility of the mobile rods 22 with respect to fixed rods 24. The attachment line 26 can be formed, for example, by metal wires or polymer bands. Exemplary materials that can be used to form the attachment line or lines 26 include highly elastic metals, such as (but not limited) to nitinol and spring metals such as spring stainless steel, or highly elastic polymers, such as (but not limited to) monofilament PEEK, a liquid crystal polymer, or PET. In some embodiments, the attachment line 26 can range in thickness from about 0.03 millimeters to about 0.10 millimeters. However, the attachment line can be other thicknesses without deviating from the scope of the disclosure.

The outer cover 16, shown in FIG. 1, can be attached to the underlying inner cylindrical structure 20 by a variety of methods, including but not limited to laminating, gluing, melting, or sewing. The outer cover 16 can be attached to the fixed rods 24 of the inner cylindrical structure 20. In some embodiments, the outer cover 16 can be attached to the connection points 28 between the fixed rods 24 and the attachment line 26.

Figure 6:
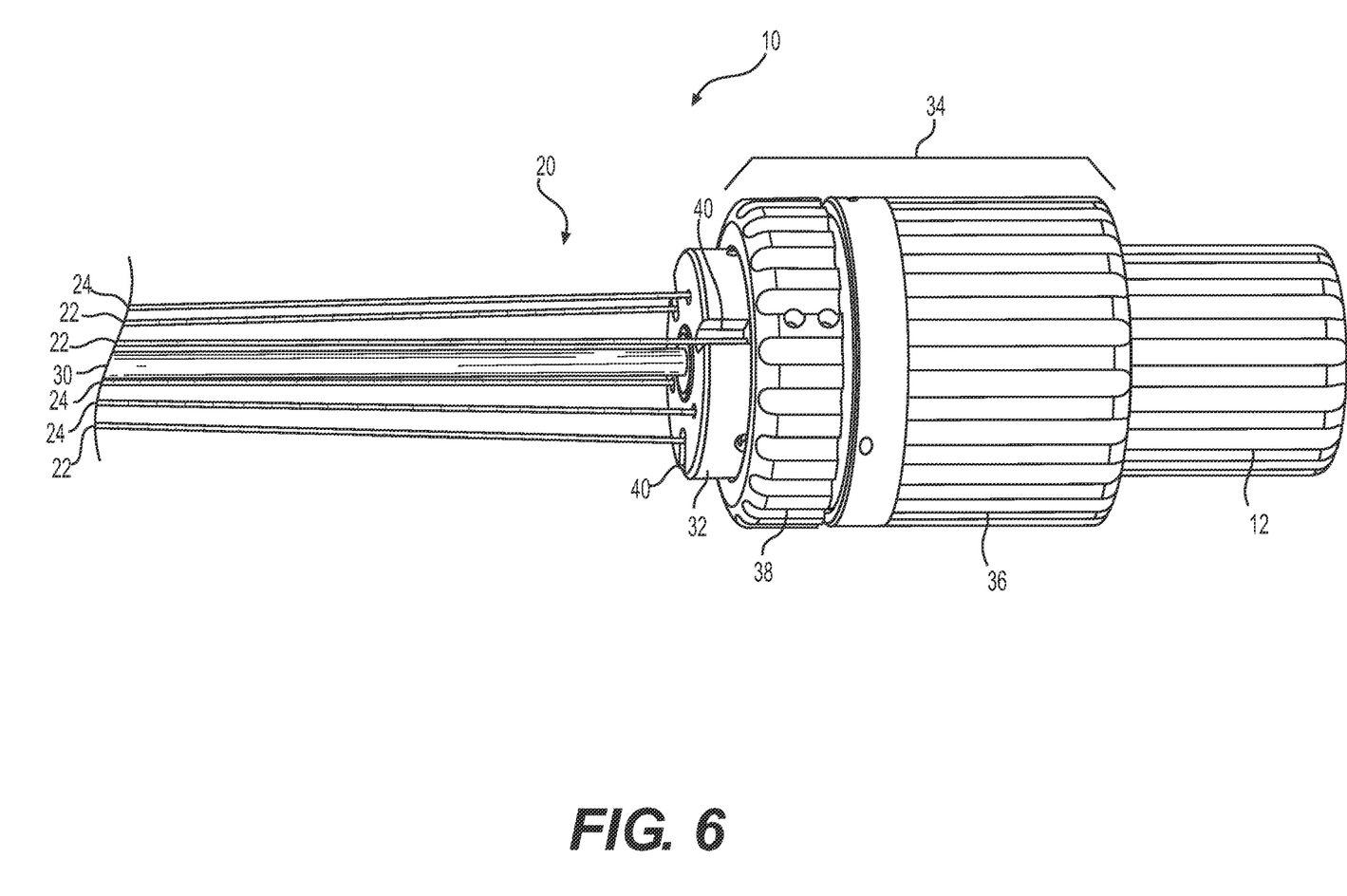
FIG. 6 shows a perspective view of a handle of an embodiment of the active introducer sheath system.
Figure 7:
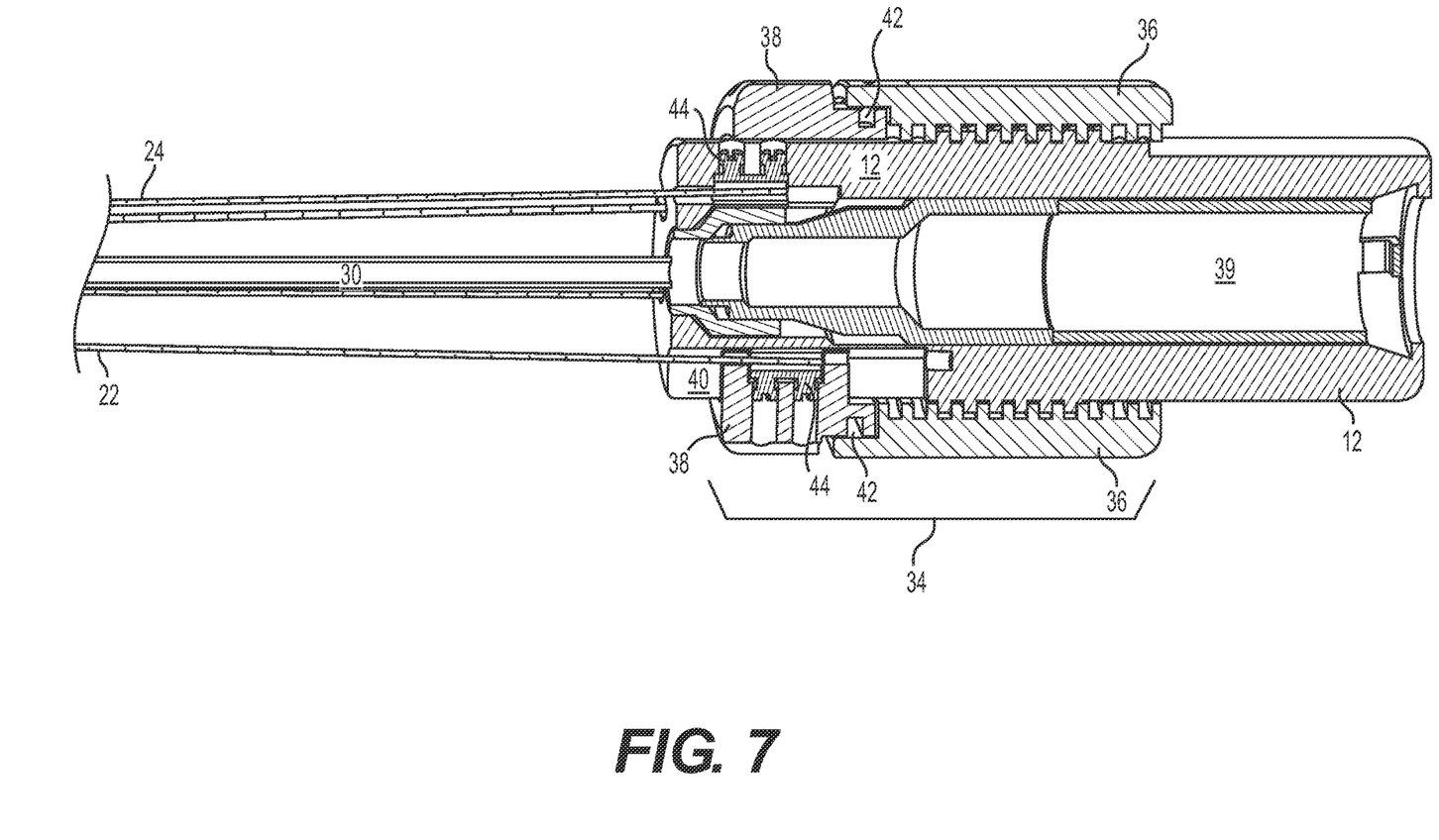
FIG. 7 shows a cross sectional view of the handle of FIG. 6.

FIG. 6 depicts the connection of the inner cylindrical structure 20 to the handle 12 of an active introducer sheath system 10. The introducer sheath system 10 is shown in a partially collapsed configuration. A partially collapsed configuration can be used to limit contact between elongate rods 22, 24 and inner tubing 30, thereby reducing the friction encountered by a passing prosthetic device. Sheath 14 is depicted without an outer cover 16 to better visualize the workings of the inner cylindrical structure 20. The elongate rods 22, 24 of the inner cylindrical structure 20 are arranged cylindrically around an inner tubing 30 at the base 32 of the sheath 14, as shown in FIG. 7. When the sheath 14 is collapsed or partially collapsed, the elongate rods 22, 24 taper inward toward the inner tubing 30 because their proximal portions are embedded within the handle 12. The smallest collapsed diameter of sheath 14 is therefore realized at a location more distal than is shown in FIGS. 6 and 7. The radial location of elongate rods 22, 24 within the handle can be varied, such that the rods are fixed closer or farther from inner tubing 30 as needed for a particular application. During a procedure, the elongate rods 22, 24 and inner tubing 30 enter the body, while base 32 and handle 12 remains outside of the body. As such, the structure and dimensions of the handle 12 can be altered to suit a particular application. FIGS. 6 and 7 are described as one exemplary embodiment.

The base 32 shown in FIG. 6 comprises notches 40 to permit the elongate mobile rods 22 to move in a radial direction, which occurs when the tension in the attachment line 26 draws them closer to the fixed rods 24. In the embodiment depicted in FIG. 6, the handle 12 is encircled by a screw type translation mechanism 34 that includes a rotating nut 36 and a distal sliding ring 38.

FIG. 7 shows a longitudinal cross section of the handle 12 and translation mechanism 34 shown in FIG. 6. Handle 12 comprises a central lumen 39, through which the shaft 122 and prosthetic device of a delivery apparatus 110 can be passed. Central lumen 39 is sized to receive and enable the passage of the prosthetic device through to inner tubing 30. The inner tubing 30 of sheath 14, which extends distally from the central lumen 39 of the handle 12, is made of a highly elastomeric material to guide and permit the passage of the delivery apparatus shaft carrying the prosthetic device. For example, in some embodiments, the inner tubing 30 can be formed of polyurethane. An inner tubing 30 formed of polyurethane can stretch to a diameter up to 300% greater than its original diameter to facilitate the passage of the prosthetic device. Alternatively, the inner tubing 30 of sheath 14 can be made of a non-elastic material that wrinkles when in the collapsed state.

Elongate fixed rods 24 are embedded in the distal portion of handle 12. In some embodiments, connector pieces 44 help to secure the proximal ends of the elongate fixed rods 24 within the handle 12. In the depicted embodiment, the proximal portions of elongate mobile rods 22 are embedded within the distal sliding ring 38 of the translation mechanism 34. Connector pieces 44 can be used to secure the proximal ends of the elongate mobile rods 22 to the translation mechanism 34. Rotating nut 36 is threadably engaged to handle 12, such that it can be axially translated along the handle upon rotation. The rotating nut 36 is attached to the elongate mobile rods 22 via the distal sliding ring 38, such that rotation of the nut 36 moves the elongate mobile rods 22 in an axial direction. The distal sliding ring 38 depicted in FIG. 7 has traveled a portion of the length of notch 40 to partially collapse sheath 14. As the distal sliding ring 38 continues to travel within notch 40, distal regions of sheath 14 will continue to narrow in diameter as the tension between the mobile elongate rods 22 and the fixed elongate rods 24 increases.

In the embodiment depicted, the rotating nut 36 and the sliding ring 38 are engaged by a circumferentially extending interlocking connection feature 42. The interlocking connection feature 42 includes a ridge extending from the rotating nut 36 and engaging a slot on distal ring 38. However, other embodiments could include alternative mechanisms to attach distal sliding ring 38 to rotating nut 36. Other translation mechanisms are also possible, including but not limited to other screw-type mechanisms, or hydraulic mechanisms, or slider mechanisms. The translation mechanism can be configured to expand the inner cylindrical structure by pulling the elongate mobile rods 22 or by pushing the elongate mobile rods 22.

In an alternative embodiment, elongate rods 22, 24 can be embedded within walls of sheath 14, i.e. between the outer cover 16 and an inner layer that replaces the inner tubing 30 shown in FIG. 7. In this embodiment, the fixed elongate rods 24 can be attached at various points along their length to the outer cover 16 and to the inner layer, whereas the mobile elongate rods 22 and the attachment line 26 are free to move to enable expansion and collapse of the sheath 14 as described above.

Methods of delivering a prosthetic device to a patient via an active introducer sheath system are also disclosed herein. The methods include moving the prosthetic device through the introducer sheath system 10 and into a patient's vasculature. Generally, during use, the sheath 14 shown in FIG. 1 is passed through the skin of patient (usually over a guidewire) such that the distal end region of the sheath 14 is inserted into a vessel, such as a femoral artery, and then advanced to a wider vessel, such as the abdominal aorta. The translation mechanism 34 at the handle 12 is then activated, pushing or pulling the set of elongate mobile rods 22 axially with respect to the elongate fixed rods 24 and lowering an internal tension in the attachment line 26. This release of the internal tension in attachment line 26 enables the inner cylindrical structure 20 to expand in diameter. In some implementations, the inner diameter of the inner cylindrical structure 20 is expanded to a wider diameter than the greatest outer diameter of the prosthetic device, minimizing the frictional push force encountered when delivering the prosthetic device. The delivery apparatus shaft 122 shown in FIG. 2 and the prosthetic device are then inserted through the central lumen 39 of the handle 12. The prosthetic device on shaft 122 is pushed through stretchable inner tubing 30 and advanced through the patient's vasculature until the prosthetic device is delivered to the implantation site and implanted within the patient.

Once the prosthetic device has passed the sheath 14 on its way to the implantation site, the sheath 14 can be contracted, or reduced in diameter, to reduce forces on the blood vessel walls during the implantation procedure. To contract the inner cylindrical structure, the translation mechanism moves the elongate mobile rods 22 in the reverse direction, thereby increasing the tension in attachment line 26. Advantageously, the outer diameter of the inner cylindrical structure 20 can be decreased back to its original outer diameter (the outer diameter prior to passage of the prosthetic device). Once the implantation procedure is complete, the active sheath 14 can again be expanded to retrieve the delivery apparatus 110. Advantageously, the diameter of the active sheath 14 is precisely controlled by the practitioner, and can be widened and contracted to accommodate any situations that arise during the procedure.

As described above, the active introducer system 10 and delivery apparatus 110 can be used to deliver, remove, repair, and/or replace a prosthetic device. In one example, a heart valve (in a crimped or compressed state) can be placed on the distal end portion of an elongated delivery apparatus shaft 122 and inserted into the sheath 14. Next, the shaft 122 and heart valve can be advanced through the patient's vasculature to the treatment site, where the valve is implanted.

Beyond transcatheter heart valves, the active introducer sheath system 10 can be useful for other types of minimally invasive surgery, such as any surgery requiring introduction of an apparatus into a subject's vessel. For example, the active introducer sheath system 10 can be used to introduce other types of delivery apparatus for placing various types of intraluminal devices (e.g., stents, stented grafts, balloon catheters for angioplasty procedures, etc.) into many types of vascular and non-vascular body lumens (e.g., veins, arteries, esophagus, ducts of the biliary tree, intestine, urethra, fallopian tube, other endocrine or exocrine ducts, etc.).

Although the foregoing embodiments of the present disclosure have been described in some detail by way of illustration and example for purposes of clarity and understanding, it will be apparent to those skilled in the art that certain changes and modifications may be practiced within the spirit and scope of the present disclosure. It is intended that the scope of the present invention herein disclosed should not be limited by the particular disclosed embodiments described above, but should be determined only by a fair reading of the claims that follow.

What is claimed is:

1. An active introducer sheath system including:
    a handle comprising a translation mechanism including:
        a rotating nut threadably engaged with the handle and axially movable along the handle upon rotation; and
    a sheath comprising a cylindrical structure including:
        a fixed rod, a proximal portion of the fixed rod fixedly attached to the handle;
        a mobile rod, a proximal portion of the mobile rod attached to the translation mechanism such that rotation of the rotating nut moves the mobile rod in an axial direction;
    wherein the fixed rod and the mobile rod are coupled such that activation of the translation mechanism causes the mobile rod to move axially with respect to the fixed rod, thereby changing a diameter of the cylindrical structure from a first diameter to a second diameter, wherein the second diameter is different from the first diameter.

2. The active introducer sheath system of claim 1, wherein the translation mechanism further includes a sliding ring rotatably coupled to the rotating nut,
wherein the rotating nut is positioned proximally of the sliding ring and engages the sliding ring to translate axially along the handle.

3. The active introducer sheath system of claim 2, wherein rotation of rotating nut causes the rotating nut and sliding ring to translate axially along the handle.

4. The active introducer sheath system of claim 2, wherein the mobile rod is attached to the rotating nut via the sliding ring such that rotation of the rotating nut moves the mobile rod in the axial direction.

5. The active introducer sheath system of claim 4, wherein the proximal portion of the mobile rod is coupled to the sliding ring,
wherein the proximal portion of the fixed rod is coupled to the handle,
wherein rotation of the rotating nut causes the sliding ring and mobile rod to translate axially along the handle while an axial position of the fixed rod remains constant.

6. The active introducer sheath system of claim 2, wherein the handle includes a body member including a threaded portion, where the rotating nut extends around at least a portion of the body member of the handle, and the rotating nut is threadably engaged with the handle at the threaded portion,
wherein the sliding ring extends around at least a portion of the body member.

7. The active introducer sheath system of claim 2, further including:
a first connector piece securing the proximal portion of the fixed rod with the handle, and
a second connector piece securing the proximal portion of the mobile rod with the translation mechanism.

8. The active introducer sheath system of claim 7, wherein the translation mechanism further includes a sliding ring rotatably coupled to the rotating nut,
wherein rotation of rotating nut causes the rotating nut and sliding ring to translate axially along the handle,
wherein the first connector piece is coupled to the handle and the second connector piece is coupled to the sliding ring, such that rotation of the rotating nut causes the sliding ring, second connector piece and mobile rod to translate axially along the handle.

9. The active introducer sheath system of claim 2, wherein the rotating nut is coupled to the sliding ring at a circumferentially extending connection feature.

10. The active introducer sheath system of claim 9, wherein the connection feature includes a ridge extending from the rotating nut and engaging a corresponding slot on distal sliding ring.

11. The active introducer sheath system of claim 10, wherein the slot extends in a radially inward direction on the sliding ring, and the ridge extends in a radially inward direction on the rotating nut.

12. The active introducer sheath system of claim 1, wherein the fixed rod is coupled to the mobile rod with an attachment line.

13. The active introducer sheath system of claim 12, wherein axial movement of the mobile rod in a direction increases tension on the attachment line such that a spacing between the mobile rod and fixed rod is reduced, changing a radial location of mobile rod with respect to the fixed rod and reducing the diameter of the cylindrical structure.

14. The active introducer sheath system of claim 12, wherein axial movement of the mobile rod in a direction decreases tension on the attachment line such that spacing between the mobile rod and fixed rod is reduced, changing a radial location of mobile rod with respect to the fixed rod and reducing the diameter of the cylindrical structure.

15. The active introducer sheath system of claim 12, wherein the attachment line comprises a plurality of rings, each ring of the plurality of rings connects the fixed rod with the mobile rod.

16. The active introducer sheath system of claim 12, wherein the attachment line comprises a coil that connects the fixed rod and the mobile rod.

17. The active introducer sheath system of claim 12, wherein the attachment line attaches to the fixed rod and the mobile rod at a series of connection points.

18. The active introducer sheath system of claim 1, further comprising an outer cover extending around the cylindrical structure, where the fixed rod is coupled to the outer cover.

19. The active introducer sheath system of claim 1, further including a set of elongate fixed rods arranged cylindrically, wherein each fixed rod of the set of elongate fixed rods comprises a proximal portion that is fixedly attached to the handle; and
further including a set of elongate mobile rods arranged cylindrically and comingled with the set of elongate fixed rods, wherein each mobile rod of the set of elongate mobile rods comprises a proximal portion that is attached to the translation mechanism;
wherein the set of elongate fixed rods and the set of elongate mobile rods are coupled such that activation of the translation mechanism causes the set of elongate mobile rods to move axially with respect to the set of elongate fixed rods, thereby changing the diameter of the cylindrical structure from the first diameter to the second diameter.

20. The active introducer sheath system of claim 19, wherein each fixed rod of the set of elongate fixed rods is positioned adjacent to a mobile rod of the set of elongate mobile rods in a circumferential direction around the sheath.

* * * * *